United States Patent [19]
Budge et al.

[11] Patent Number: 4,965,378
[45] Date of Patent: Oct. 23, 1990

[54] VAPOR-PHASE HYDROGENATION OF MALEIC ANHYDRIDE TO TETRAHYDROFURAN AND GAMMA-BUTYROLACTONE

[75] Inventors: John R. Budge, Cleveland Heights; Thomas G. Attig, Aurora, both of Ohio

[73] Assignee: The Standard Oil Company, Cleveland, Ohio

[21] Appl. No.: 370,925

[22] Filed: Jun. 23, 1989

Related U.S. Application Data

[63] Continuation-in-part of Ser. No. 231,940, Aug. 15, 1988, abandoned, which is a continuation-in-part of Ser. No. 137,042, Dec. 23, 1987, abandoned.

[51] Int. Cl.$^5$ .......................................... C07D 307/08
[52] U.S. Cl. ................................................... 549/508
[58] Field of Search ........................................ 549/508

[56] References Cited

U.S. PATENT DOCUMENTS

| | | | |
|---|---|---|---|
| 3,853,922 | 12/1974 | Yamaguchi et al. | 549/508 |
| 3,894,054 | 7/1975 | Miya | 549/508 |
| 4,048,196 | 9/1977 | Broeck et al. | 549/508 |
| 4,810,807 | 3/1989 | Budge et al. | 549/508 |

*Primary Examiner*—Richard L. Raymond
*Attorney, Agent, or Firm*—D. P. Yusko; D. J. Untener; L. W. Evans

[57] ABSTRACT

Tetrahydrofuran and optionally gamma-butyrolactone are prepared from at least one of maleic anhydride or succinic anhydride by catalytically hydrogenating vaporous maleic anhydride or vaporous succinic anhydride in the presence of hydrogen and a catalyst comprising the mixed oxides of copper, zinc and aluminum.

13 Claims, No Drawings

VAPOR-PHASE HYDROGENATION OF MALEIC ANHYDRIDE TO TETRAHYDROFURAN AND GAMMA-BUTYROLACTONE

REFERENCE TO RELATED APPLICATIONS

This is a continuation-in-part of U.S. application Ser. No. 231,940 filed Aug. 15, 1988, now abandoned, which was a continuation-in-part of U.S. application Ser. No. 137,042, filed Dec. 23, 1987, now abandoned.

BACKGROUND OF THE INVENTION

1. Field of the Invention

This invention relates to the preparation of tetrahydrofuran and gamma-butyrolactone from at least one of maleic anhydride or succinic anhydride. In one embodiment this invention relates to a single stage process for the vapor phase hydrogenation of maleic anhydride or succinic anhydride in the presence of a catalyst comprising the mixed oxides of copper, zinc and aluminum to produce high yields of tetrahydrofuran. In another embodiment, this invention relates to a single stage process for the vapor phase hydrogenation of maleic anhydride or succinic anhydride in the presence of a catalyst comprising the mixed oxides of copper, zinc and aluminum to produce high yields of tetrahydrofuran and gamma-butyrolactone.

2. Description of the Prior Art

Tetrahydrofuran is a useful solvent for natural and synthetic resins and is a valuable intermediate in the manufacture of a number of chemicals and plastics. Gamma-butyrolactone is an intermediate for the synthesis of butyric acid compounds, polyvinylpyrrolidone and methionine. Gamma-butyrolactone is a useful solvent for acrylate and styrene polymers and also a useful ingredient of paint removers and textile assistants.

It is known in the art that tetrahydrofuran and gamma-butyrolactone may be produced by a number of different methods. For example, tetrahydrofuran is produced by the dehydration of 1,4-butanediol and gamma-butyrolactone can be prepared by the dehydrogenation of 1,4-butanediol. Specifically, most tetrahydrofuran and gamma-butyrolactone is manufactured in a multi-step sequence starting with the reaction of acetylene and formaldehyde in the presence of a cuprous acetylide complex to form butynediol. The butynediol is reduced to butanediol, which is dehydrated to tetrahydrofuran and dehydrogenated to gamma-butyrolactone as indicated above.

In addition, tetrahydrofuran and gamma-butyrolactone can be prepared by catalytic hydrogenation of maleic acid, fumaric acid and succinic acid, their respective anhydrides and ester derivatives.

The instant invention focuses on the production of tetrahydrofuran and tetrahydrofuran with gamma-butyrolactone from maleic anhydride. A multi-step process for producing tetrahydrofuran and gamma-butyrolactone in addition to 1,4-butanediol from maleic anhydride is described in U.S. Pat. No. 4,584,419. In this patent the ethyl diester of maleic anhydride is produced and then hydrogenated in the presence of a copper-chromite catalyst to yield minor quantities of tetrahydrofuran and larger quantities of 1,4-butanediol and gamma-butyrolactone.

Tetrahydrofuran and gamma-butyrolactone are derived from maleic anhydride or succinic anhydride using nickel base catalysts in U.S. Pat. No. 3,853,922 and U.S. Pat. No. 3,829,448.

Lastly, U.S. Pat. No. 3,894,054 describes a vapor phase process for the conversion of maleic anhydride to tetrahydrofuran using a two component catalyst system consisting of a Cu/Zn/Cr catalyst and a silica-alumina catalyst which had been calcined at approximately 1000° C.

An object of this invention is to provide a process for producing tetrahydrofuran and optionally gamma-butyrolactone from maleic anhydride and succinic anhydride in high yields using a single component catalyst and without first esterifying the anhydride. Another object is to provide an efficient catalyst which will produce tetrahydrofuran and optionally gamma-butyrolactone in high yields in a single hydrogenation step with less by-products. Still another object is to provide a novel hydrogenation catalyst which maintains high activity over time.

SUMMARY OF THE INVENTION

Maleic anhydride is catalytically hydrogenated to produce tetrahydrofuran or tetrahydrofuran and gamma-butyrolactone in a continuous single stage process. It has been discovered that high yields of tetrahydrofuran or the combination of tetrahydrofuran and gamma-butyrolactone are achieved when the hydrogenation catalyst comprises the mixed oxides of copper, zinc and aluminum.

DETAILED DESCRIPTION OF THE INVENTION

Maleic anhydride or succinic anhydride are hydrogenated in the vapor phase by passing a mixture of a hydrogen containing gas and the anhydride over a hydrogenation catalyst comprising the mixed oxides of copper, zinc and aluminum.

Reactants

At least one of maleic anhydride or succinic anhydride is fed continuously together with hydrogen, and without further treatment or working-up, over a hydrogenation catalyst.

Maleic anhydride,

HC=CHC(O)OC(O), is derived from a number of sources. Mostly maleic anhydride is produced by passing a mixture of benzene or butane over a vanadium oxide catalyst at about 450° C. Maleic anhydride is also produced as a by-product from the manufacture of phthalic anhydride from naphthalene or by the catalytic oxidation of butylenes. Succinic anhydride,

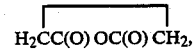
H$_2$CC(O) OC(O) CH$_2$, may be produced by the dehydration of succinic acid but is most commonly produced by the direct hydrogenation of maleic anhydride.

Typically, the hydrogen (H$_2$) containing gas is commercially pure hydrogen. However, the hydrogen containing gas in addition to hydrogen (H$_2$) may also contain nitrogen (N$_2$), oxygen (O$_2$), any gaseous hydrocarbon (e.g. methane), as well as gaseous oxides of carbon, (e.g. carbon monoxide, carbon dioxide).

Catalyst

The instant process for the hydrogenation of at least one of maleic anhydride or succinic anhydride to produce tetrahydrofuran is characterized by the use of a hydrogenation catalyst comprising the mixed oxides of copper, zinc and aluminum.

Typically, the hydrogenation catalyst comprising the mixed oxides of copper, zinc and aluminum is of the general formula:

$$Cu_1Zn_bAl_cM_dO_x$$

where M is at least one element selected from Groups IIA and IIIA, Group VA, Group VIII, Ag, Au, Groups IIIB thru VIIB, the Lanthanum Series, and Actinium Series of the Period Table of Elements
 $0.001 < b < 500$;
 $0.001 < c < 500$;
 $0 \leq d < 200$; and
 x is the number of oxygen atoms necessary to satisfy the valency requirements of the other elements.

As used herein, the Periodic Table of Elements refers to the commonly accepted version as appears in *The Condensed Chemical Dictionary*, 10th Edition, G. G. Hawley, Van-Nostrand Reinhold Company (1981), p. 789. Preferably, the catalyst identified by the above formula contains greater than 10 wt percent of aluminum and more preferably greater than 15 wt percent of aluminum.

The characterization of the catalyst as a "mixed oxide" does not imply that the catalyst cannot contain metallic components. Typically, prior to reduction there are no metallic components in the catalyst. However, it is theorized that the reduction of certain metal oxides (e.g. copper oxide) will produce some metallic (i.e. non-oxide) component in the catalyst composition. Consequently, the reduced version of the catalyst may contain metallic copper in addition to the oxides of copper, zinc and aluminum. Additionally, the catalyst may also contain nitrogen and phosphorus (i.e. where "M" is a Group V element), and compounds containing such elements are typically not referred to as "oxides". Nevertheless such nitrogen or phosphorus containing compositions contain the mixed oxides of copper, zinc and aluminum and are within the meaning of the "catalytically active oxides" or "mixed oxides" as used herein.

Copper chromium containing hydrogenation catalysts are known in the art. The catalyst shown by the above formula optionally contains oxidized or metallic chromium, iron, nickel and cobalt; however, an excellent catalyst of the above formula may be produced with no chromium, no iron, no nickel or no cobalt contained in the catalyst. Preferably the catalyst contains no metallic nickel. Lastly, in the absence of chromium, in the catalyst, "M" in the above formula may include at least one of Si, Ge, Sn, or Pb in addition to or in place of any of the previous designated elements for "M".

Typically, the catalysts of the present invention may be prepared by conventional techniques including coprecipitation techniques such as those described in *Preparation of Catalysts III*, Hoffstadt et al., Elsevier Science Publishers B.V., (1983) pgs. 709–721. In general, this technique comprises coprecipitation of an aqueous metal nitrate solution at elevated temperatures with an alkali or ammonium carbonate or bicarbonate. The precipitated material is then filtered off, washed and then dried at elevated temperatures (120° C.) and calcined at a temperature of 350°–400° C. The catalyst could also be impregnated with one or more promoter elements prior to the calcination step. Alternatively, promoter elements could be incorporated in the precipitation step.

Prior to use, the catalyst may be reduced at temperatures between 150°–500° C. by flowing hydrogen, or hydrogen mixed with an inert gas (e.g. nitrogen) over the catalyst. Other reducing gas mixtures may also be used, such as carbon monoxide, carbon monoxide/hydrogen, and carbon monoxide/water. The reduction may be carried out at atmospheric or elevated pressures.

Typically, sufficient catalyst is packed into a fixed-bed or fluid-bed reactor and the reactants passed over and/or through a catalyst bed for continuous operation. In a batch operation, typically 0.1 and about 10 wt %, and preferably between about 1 and about 5 wt % of catalyst is used based upon the weight of the maleic anhydride or succinic anhydride to be converted.

Process Parameters

At least one of maleic anhydride or succinic anhydride (in the absence of added water) are co-fed with a hydrogen-containing gas over the hydrogenation catalyst, at elevated temperature and pressures. The hydrogen to anhydride molar feed ratio may vary from about 10:1 to about 1000:1, and is preferably between about 50:1 and 500:1.

The hydrogen containing gas can be introduced into the hydrogenation apparatus together with the maleic anhydride or succinic anhydride mixture, co-currently or counter-currently. Typically, the anhydride is vaporized in a hot hydrogen containing gas stream and this mixture is then passed over the hydrogenation catalyst. In order to enhance process economics, unreacted hydrogen discharged from the hydrogenation reaction may be recycled to the hydrogenation furnace.

The quality of the results of the hydrogenation reaction is partially dependent on the throughput of the anhydride-hydrogen mixture over the catalyst. The throughput for the successful performance of the reaction can vary within wide limits. For example, the maleic anhydride or succinic anhydride liquid hourly space velocity (LHSV) is between about 0.01 and 10 per hour, the hydrogen containing gas hourly space velocity (GHSV) is between about 100 to 500,000 per hour. The LHSV and GHSV rates used herein are the feed rates of the reactants prior to vaporization of the anhydride. At these rates the contact time is considerably less than one hour. Preferably contact times are less than 1 minute and more preferably less than 20 seconds. Typical reaction times are between 2 and 10 seconds.

The vaporous feed mixture is contacted with the hydrogenation catalyst at pressures of 1 to 500 atmospheres, preferably at 1 to 100 atmospheres, more preferably at about 1 to 50 atmospheres hydrogen pressure. Suitable reaction temperatures are 200° C. to 400° C. and are preferably 220° C. to 300° C.

Hydrogenation furnaces of conventional construction can be used for carrying out the process of this invention, provided that they are designed for the requisite temperatures and pressures and are made of acid-resistant material. Further, the process may be carried out in a variety of reactors including fixed-bed and fluid-bed systems.

The reaction products (predominantly tetrahydrofuran or tetrahydrofuran and gamma-butyrolactone) are advantageously separated by fractional distillation. By-products which are formed in small amounts or unreacted feed, such as, for example, succinic anhydride are advantageously returned to the hydrogenation stage. Small proportions of acidic by-products in the product can be removed by treatment with alkali before distillation.

Using the process of this invention, maleic anhydride or succinic anhydride is converted virtually quantitatively (i.e., 100 percent conversion of feed to products and by-products) in a simple reaction, without the build-up of coke or tar inside the reactor. The yields of tetrahydrofuran achieved are greater than 90 mole percent, e.g., 91-98 mole percent. The formation of non-utilizable by-products is slight. Tetrahydrofuran which is more than 99.5 percent pure can be recovered and separated from the reaction products by fractional distillation.

Gamma-butyrolactone is an intermediate in the hydrogenation of maleic anhydride or succinic anhydride to tetrahydrofuran. It has been theorized that the existence of succinic anhydride in the reactor strongly inhibits the adsorption of the gamma-butyrolactone onto the catalyst. This means that less tetrahydrofuran is formed when succinic anhydride is concentrated at the catalyst; but as the amount of succinic anhydride decreases, the rapid formation of tetrahydrofuran begins. Consequently, if the reaction is stopped just before the rapid transformation of gamma-butyrolactone to tetrahydrofuran or if the rate at which gamma-butyrolactone is transformed to tetrahydrofuran is slowed, then more gamma-butyrolactone will appear in the product. Methods for accomplishing this and controlling the proportions of tetrahydrofuran and gamma-butyrolactone produced include adjusting the process parameters of (i) temperature and/or (ii) pressure, and/or (iii) maleic anhydride and succinic anhydride throughput, and/or (iv) maleic anhydride and succinic anhydride partial pressure. For example, at the point in the reaction where significant production of both tetrahydrofuran and gamma-butyrolactone are occurring, (i) increasing the temperature, while maintaining other reaction parameters constant, will favor the production of tetrahydrofuran; (ii) increasing the throughput, while maintaining other reaction parameters constant, will favor gamma-butyrolactone production; and (iii) increasing the partial pressure of the anhydride, while maintaining the overall anhydride throughput and the other reaction parameters constant, will favor gamma-butyrolactone production. Consequently, gamma-butyrolactone in addition to tetrahydrofuran may be produced by the instant invention in recoverable quantities approaching a 1:4 ratio of tetrahydrofuran to gamma-butyrolactone and combined yields of 90 mole percent or greater.

Although the preceding description is given in terms of a continuous process, if desired, the process of this invention may be carried out in batch mode employing conditions corresponding to those specified above. Without further elaboration, it is believed that one skilled in the art can, using the preceding description, utilize the present invention to its fullest extent.

SPECIFIC EMBODIMENT

The following preferred embodiments are to be construed as merely illustrative, and not limitative of the remainder of the disclosure in any way whatsoever. The percent yields in all examples result from 100 percent conversion of the feed to the products and by-products.

Example 1

A commercially available catalyst comprising the mixed oxides of copper, zinc, aluminum and chromium is employed in Example 1. The oxidized form of this catalyst is of the general formula $CuO/ZnO/Al_2O_3/Cr_2O_3$. The nominal compositions of the unreduced catalyst is as follows:

| | |
|---|---|
| Copper Oxide | 40-50 wt % |
| Zinc Oxide | 10-20 wt % |
| Alumina | 20-30 wt % |
| Chrome Oxide | 1-5 wt % |

This catalyst has an empirical formula of $Cu_{1.0}Al_{1.2}Zn_{0.4}Cr_{0.04}O_x$.

The catalyst was obtained in ⅛" pellet form. The pellets were ground and sieved to obtain 10/30 mesh fractions which were used for catalyst testing.

20 cc of the $CuO/ZnO/Al_2O_3/Cr_2O_3$ catalyst (21.4 g) was loaded into a 40 cc tubular stainless steel reactor. The catalyst was reduced at 250° C. and atmospheric pressure, with a gas mixture of 5% $H_2$ in $N_2$ flowing over the catalyst at a rate of 1 standard liters per minute (SLM).

After reduction, the system was pressurized to 600 psig and a mixture of vaporized maleic anhydride in hydrogen was passed over the catalyst. The $H_2$/MAH mixture was prepared by pumping molten maleic anhydride in a stream of hydrogen in a vaporizer at 155° C. The details and results of the catalyst testing between 235° C. and 250° C. are summarized in Table I below:

TABLE I

| Hydrogenation of MAH over $CuO/ZnO/Al_2O_3/Cr_2O_3$ | | | | |
|---|---|---|---|---|
| Temperature (°C.) | 235 | 240 | 250 | 250 |
| MAH Partial Pressure (atm) | 0.139 | 0.131 | 0.127 | 0.208 |
| Contact Time (sec) | 13.5 | 8.4 | 5.9 | 6.1 |
| $H_2$ GHSV $(h^{-1})$ | 5840 | 9320 | 12520 | 12505 |
| MAH LHSV $(h^{-1})$ | 0.068 | 0.101 | 0.135 | 0.216 |
| Percent Yield | | | | |
| THF | 92 | 98 | 95 | 96 |
| Butane | 0.7 | 0.8 | 2.3 | 1.2 |
| Butanol | 2.5 | 2.0 | 2.8 | 2.2 |
| Propanol | 0.2 | 0.16 | 0.22 | 0.26 |
| Methanol | 0.05 | 0.04 | 0.05 | 0.04 |

Pressure = 600 psig

Pressure=600 psig

Table I illustrates that the process of the instant invention produces high yields of tetrahydrofuran over a range of throughputs and maleic anhydride to hydrogen ratios.

Example 2

The $CuO/ZnO/Al_2O_3/Cr_2O_3$ hydrogenation catalyst, as used in Example 1, was obtained in ⅛" pellet form. The pellets were calcined at 450° C. and then ground and meshed to obtain a 20/30 mesh fraction. 5 cc of this catalyst was diluted with 15 cc of quartz chips of the same mesh size and then loaded into a 40 cc tubular stainless steel reactor. The catalyst was reduced at 250°–270° C. in a 5% $H_2/N_2$ gas mixture flowing at 1 SLM.

Catalyst testing was carried out at 300 psig and 250°–270° C. Maleic anhydride was vaporized into a hydrogen stream at 155° C. This mixture was then transferred via a heated line to the reactor. The test results are summarized in Table II below:

TABLE II

Hydrogenation of MAH over $CuO/ZnO/Al_2O_3/Cr_2O_3$ in Quartz Catalyst

| TOS h | Temperature °C. | LHSV $h^{-1}$ | GHSV $h^{-1}$ | % YIELDS | | | | | |
|---|---|---|---|---|---|---|---|---|---|
| | | | | THF | GBL | SAH | BDO | ROH | GAS |
| 51 | 270 | 0.81 | 66100 | 64.1 | 23.7 | 2.5 | 0.6 | 2.5 | 0.41 |
| 194 | 250 | 0.27 | 22025 | 36.3 | 52.4 | 8.6 | 0.3 | 1.2 | 0.25 |
| 290 | 250 | 0.27 | 22025 | 31.4 | 50.6 | 10.3 | 0.2 | 1.2 | 0.25 |
| 314 | 250 | 0.27 | 22025 | 31.9 | 51.3 | 10.4 | 0.3 | 1.2 | 0.25 |

TOS = Time on Stream
THF = Tetrahydrofuran
GBL = Gamma-Butyrolactone
SAH = Succinic Anhydride
BDO = 1,4-Butanediol
ROH = Propanol and Butanol
GAS = $CH_4$, $CO_2$ and Butane Table II illustrates that high yields of both tetrahydrofuran and gamma-butyrolactone are achievable in the instant process. Also, the above data illustrates that less tetrahydrofuran and more gamma-butyrolactone can be produced in the instant process by adjusting the process parameters.

Example 3

The $CuO/ZnO/Al_2O_3/Cr_2O_3$ hydrogenation catalyst, as used in Example 1, was obtained in $\frac{1}{8}''$ pellet form. The pellets were calcined at 450° C. and then ground and meshed to obtain a 20/30 mesh fraction. 5 cc of this catalyst was diluted with 15 cc of a low surface area alumina (Harshaw Al-390T). The alumina, obtained as $\frac{1}{8}''$ pellets was ground and meshed to give a 20/30 mesh fraction. The catalyst and alumina were loaded into a 40 cc tubular stainless steel reactor. The catalyst was then reduced and tested as described in Example 2. The test results are summarized in Table III below.

TABLE III

Hydrogenation of MAH over $CuO/ZnO/Al_2O_3/Cr_2O_3$ in Alumina Catalyst

| TOS h | Temperature °C. | LHSV $h^{-1}$ | GHSV $h^{-1}$ | % YIELDS | | | | | |
|---|---|---|---|---|---|---|---|---|---|
| | | | | THF | GBL | SAH | BDO | ROH | GAS |
| 349 | 265 | 0.66 | 50400 | 83.6 | 11.5 | 1.1 | 0 | 2.6 | 1.1 |
| 564 | 270 | 0.66 | 50400 | 93.7 | 1.3 | 0 | 0 | 3.7 | 1.4 |

Table III illustrates that greater yields of tetrahydrofuran are achieved by increasing the process temperature while maintaining the remaining process parameters constant.

Although the invention has been described in considerable detail through the preceding examples, these examples are for the purpose of illustration only and one skilled in the art will understand that variations and modifications can be made without departing from the spirit and scope of the invention.

The claimed invention is:

1. A continuous process for the preparation of tetrahydrofuran comprising catalytically hydrogenating a vaporous mixture consisting essentially of at least one of maleic anhydride or succinic anhydride in a hydrogen containing gas in contact with a hydrogenation catalyst, wherein the hydrogenation catalyst consists essentially of the formula:

$$Cu_1Zn_bAl_cM_dO_x$$

wherein M is at least one element selected from the group consisting of

Groups IIA and IIIA, Group VA, Group VIII, Ag, Au, Groups IIIB thru VIIB, the Lanthanum Series, and Actinium Series,
$0.001 < b < 500$;
$0.001 < c < 500$;
$0 \leq d < 200$; and
x is the number of oxygen atoms necessary to satisfy the valency requirements of the other elements, and wherein the hydrogenation catalyst contains no metallic nickel.

2. The process of claim 1, wherein tetrahydrofuran and gamma-butyrolactone are produced.

3. The process of claim 1, wherein the reaction time is less than 1 minute.

4. The process of claim 3, wherein the hydrogenation catalyst contains greater than 10 weight percent aluminum.

5. The process of claim 4, wherein the hydrogenation catalyst contains greater than 15 weight percent aluminum.

6. The process of claim 1, wherein the hydrogen to anhydride feed ratio is between about 10 to 1 and 1000 to 1.

7. The process of claim 6, wherein the hydrogen to the anhydride feed ratio is between about 50 to 1 and 500 to 1.

8. The process of claim 1, wherein the hydrogenation is conducted at a pressure about 1 to 100 atmospheres and at a temperature of about 200° C. to 400° C.

9. The process of claim 8, wherein the hydrogenation is conducted at a pressure of about 1 to 50 atmospheres and at a temperature of about 220° C. to 300° C.

10. The process of claim 1, wherein the catalyst comprises the mixed oxides of copper, zinc and aluminum in the absence of chromium.

11. The process of claim 1, wherein the catalyst comprises the mixed oxides of copper, zinc and aluminum in the absence of iron.

12. The process of claim 1, wherein the catalyst comprises the mixed oxides of copper, zinc and aluminum in the absence of cobalt.

13. A continuous process for the preparation of tetrahydrofuran comprising catalytically hydrogenating a vaporous mixture consisting essentially of at least one of maleic anhydride or succinic anhydride in a hydrogen containing gas in contact with a hydrogenation catalyst, wherein the hydrogenation catalyst consists essentially of the formula:

$$Cu_1Zn_bAl_cM_dO_x$$

wherein M is at least one element selected from the group consisting of Groups IIA and IIIA, Group VA, Group VIII, Ag, Au, Groups IIIB thru VIIB, Si, Ge, Sn, Pb, the Lanthanum Series, and Actinium Series, provided that M is not chromium, $0.001 < b < 500$;
$0.001 < c < 500$;
$0 \leq d < 200$; and x is the number of oxygen atoms necessary to satisfy the valency requirements of the other elements, and wherein the catalyst contains no metallic nickel.

* * * * *